(12) United States Patent
McKinnie et al.

(10) Patent No.: US 6,639,118 B1
(45) Date of Patent: Oct. 28, 2003

(54) ISOMERIZATION OF VINYLIDENE OLEFINS

(76) Inventors: Bonnie G. McKinnie, 261 Columbia 10 W., Magnolia, AR (US) 71753; J. Todd Aplin, 5023 Front Royal Dr., Baton Rouge, LA (US) 70817; Robert U. Lyons, 2508 Regency, Magnolia, AR (US) 71753; Clinton R. Parham, 2604 Pearce St., Magnolia, AR (US) 71753

( * ) Notice: Subject to any disclaimer, the term of this patent is extended or adjusted under 35 U.S.C. 154(b) by 0 days.

(21) Appl. No.: 10/269,301

(22) Filed: Oct. 11, 2002

(51) Int. Cl.[7] .......................... C07C 209/08; C07C 5/27
(52) U.S. Cl. ................ 585/669; 564/481; 564/482; 564/485
(58) Field of Search ................ 564/481, 482, 564/485; 585/669

(56) References Cited

U.S. PATENT DOCUMENTS

| | | | |
|---|---|---|---|
| 3,686,250 A | 8/1972 | Lanier | 260/448 A |
| 3,723,556 A * | 3/1973 | Wilhelm | 260/668 A |
| 4,024,189 A | 5/1977 | Davis | 260/585 A |
| 4,511,753 A | 4/1985 | Smith et al. | 585/856 |
| 4,587,374 A | 5/1986 | Peters | 585/670 |
| 4,710,273 A | 12/1987 | Okamoto | 203/29 |
| 4,822,911 A | 4/1989 | Fried | 560/205 |
| 4,962,226 A | 10/1990 | Fried | 560/205 |
| 4,982,024 A | 1/1991 | Lin et al. | 570/262 |
| 5,095,172 A | 3/1992 | Lanier et al. | 585/851 |
| 5,120,901 A | 6/1992 | DiLeo et al. | 585/851 |

* cited by examiner

*Primary Examiner*—Peter O'Sullivan
(74) *Attorney, Agent, or Firm*—Edgar E. Spielman, Jr.

(57) ABSTRACT

Process technology for selectively isomerizing vinylidene olefin to tri-substituted olefin is described. The vinylidene olefin, normally in admixture with other types of olefins, especially linear 1-olefins, is treated with anhydrous hydrogen bromide under anhydrous conditions and in the absence of molecular oxygen and free radical initiator. The contacting period, which can be a matter of minutes, is sufficient to selectively isomerize the vinylidene olefin to tri-substituted olefin. If the process is conducted properly, little if any hydrobromination occurs.

27 Claims, No Drawings

ISOMERIZATION OF VINYLIDENE OLEFINS

TECHNICAL FIELD

This invention relates to process technology for selective isomerization of vinylidene olefins to tri-substituted olefins, especially when the vinylidene olefins are in admixture with at least linear 1-olefins or remotely branched 1-olefins.

BACKGROUND

Mixtures of terminal olefins, commonly referred to as α-olefins, are made commercially by ethylene chain growth of aluminum alkyls followed by displacement. Such products are mainly 1-olefins having the structure:

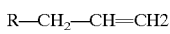

wherein R is an aliphatic hydrocarbon group. These are also referred to as "vinyl olefins". A substantial portion of the α-olefins can be in the form of "vinylidene olefins" which have the structure:

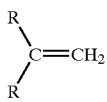

wherein both R groups are aliphatic hydrocarbon groups.

One commercially important use of such α-olefin mixtures is in the manufacture of aliphatic amines, especially alkyldimethyl amines, such as described in U.S. Pat. No. 4,024,189. In such processing, α-olefin mixtures which contain vinyl olefins and vinylidene olefins are subjected to a selective isomerization step in which vinylidene olefins are converted to tri-substituted olefins. The entire mixture of olefins is then hydrobrominated to produce brominated alkanes. The brominated alkanes in turn are selectivity dehydrobrominated whereby secondary bromoalkanes are converted to olefins leaving the primary bromoalkanes substantially unaffected. Amination of the primary bromoalkanes results in production of the desired amines.

A number of isomerization catalysts capable of selectively isomerizing vinylidene olefins to tri-substituted olefins are known. See for example U.S. Pat. No. 3,686,250. While effective, such known catalysts often possess various shortcomings. For example, some of these catalysts are expensive, some may become inactivated or poisoned by impurities thus necessitating more frequent replenishment of the catalyst than would be desired, some of them tend to cause an undesirable amount of isomerization of linear 1-olefins to linear internal olefins, and some of them tend to cause dimerization of linear 1-olefins and of vinylidene olefins, which is also undesirable.

It would be of advantage if a new, efficient and commercially feasible way of selectively isomerizing vinylidene olefins to tri-substituted olefins could be found. It would be of particular advantage if this could be accomplished by use of a catalyst which is inexpensive, readily available, not susceptible to poisoning or inactivation under appropriate reaction conditions, that does not tend to excessively isomerize linear 1-olefins to linear internal olefins, and that does not tend to cause an excessive amount of dimer formation. This invention is believed to enable the achievement of most, if not all, of these advantages.

THE INVENTION

This invention is based in part on the discovery that vinylidene olefins can be rapidly and selectively isomerized to tri-substituted olefins by use of small quantities of anhydrous HBr. Surprisingly, by use of appropriate reaction conditions (e.g., absence of molecular oxygen whether in the form of air or otherwise, and free radical initiator), hydrobromination of the olefins can be avoided when conducting this selective isomerization.

Accordingly, pursuant to one of its embodiments, this invention provides a process of isomerizing at least one vinylidene olefin to at least one tri-substituted olefin, which process comprises contacting the mixture with anhydrous hydrogen bromide under anhydrous conditions and in the absence of molecular oxygen and free radical initiator, for a period of time sufficient to isomerize vinylidene olefin to tri-substituted olefin. In this process, little if any hydrobromination occurs. Usually, but not necessarily, the process of this embodiment is performed in the presence of at least one olefin that is not a vinylidene olefin or a tri-substituted olefin. In any case, the product recovered after the contacting is enriched in tri substituted olefin.

When the isomerization is performed in the presence of linear 1-olefins or remotely branched 1-olefins, the linear 1-olefins and the remotely branched 1-olefins are substantially unaffected. Thus in this case, the process is a selective isomerization process.

Accordingly, pursuant to another of its embodiments this invention provides a process for selective isomerization of at least one $C_{10-20}$ vinylidene olefin to tri-substituted olefin in an anhydrous hydrocarbon mixture comprised of (i) at least one $C_{10-20}$ vinylidene olefin, (ii) at least one $C_{10-20}$ linear 1-olefin or (iii) at least one $C_{10-20}$ remotely-branched 1-olefin, or (iv) a combination of (i), (ii) and (iii), and optionally (v) at least one $C_{10-20}$ internal olefin or (vi) at least one saturated hydrocarbon, or (vii) both of (v) and (vi), while leaving the 1-olefins substantially unaffected during the isomerization, which process comprises contacting the mixture with anhydrous hydrogen bromide under anhydrous conditions and in the absence of molecular oxygen and free radical initiator for a period of time sufficient to selectively isomerize vinylidene olefin to tri-substituted olefin. As noted above little if any hydrobromination occurs in the process.

Another embodiment of this invention provides an improvement in a process for producing amines from a mixture of α-olefins comprising vinylidene olefins and 1-olefins, wherein:

a) the mixture of olefins is subjected to selective isomerization to convert vinylidene olefins to tri-substituted olefins;

b) the olefin mixture resulting from the isomerization is hydrobrominated to form bromoalkanes comprising 1-bromoalkanes and secondary bromoalkanes and/or tertiary bromoalkanes;

c) bromoalkanes resulting from the hydrobromination are selectively dehydrobrominated whereby 1-bromoalkanes are substantially unaffected and secondary and/or tertiary bromoalkanes present are converted to olefins;

d) bromoalkanes from c) are aminated with an amine having at least one replaceable hydrogen atom whereby the 1-bromoalkanes are converted to amine hydrobromides, and e) amine hydrobromides from d) are converted into amines.

Such a process has been commercially used. A full description of process technology of this type is present for example in U.S. Pat. No. 4,024,189. The improvement pursuant to this invention comprises effecting said selective isomerization by contacting said mixture of α-olefins with anhydrous hydrogen bromide under anhydrous conditions and in the absence of molecular oxygen and free radical initiator for a period of time sufficient to selectively isomerize vinylidene olefin to tri-substituted olefin. Use of such selective isomerization leaves the 1-olefin content of the mixture substantially unaffected and in addition, little if any hydrobromination occurs. In addition, since one of the steps of this process involves hydrobromination, a source of anhydrous HBr is already available for use in the selective isomerization. Thus, no additional raw materials are required to carry out the isomerization.

Other embodiments and features of this invention will still be further apparent from the ensuing description and appended claims.

FURTHER DETAILED DESCRIPTION

At the outset it is to be noted that the selective isomerization effected pursuant to this invention should not be confused with olefin hydrobromination processes in which anhydrous hydrogen bromide is added to an olefin mixture in order to produce brominated alkanes. A hydrobromination process is conducted in the presence of a substance functioning as a free radical initiator, and molecular oxygen such as in the form of air can function to initiate hydrobromination. Moreover, in hydrobromination processes a stoichiometric amount or an excess amount of hydrogen bromide relative to olefin is employed. In the isomerization process of this invention, air (and molecular oxygen in any mixture) is excluded from the reaction mixture, and no substance is introduced into the system to function as a free radical initiator. And, little if any hydrobromination occurs. Thus even though in a hydrobromination process, hydrogen bromide and olefin are contacted with each other, both the composition of the reaction mixture and the composition of the products of the process differ materially from the isomerization process of this invention.

To assist those who may be unfamiliar with the technology associated with α-olefins, it is believed useful to explain some of the terms that are used by those of ordinary skill in this art. Accordingly, as used herein and as used by those of ordinary skill in this art:

1) Linear 1-olefins are compounds of the formula

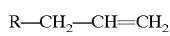

where R is a straight chain alkyl group.
2) Remotely branched 1-olefins are compounds of the formula

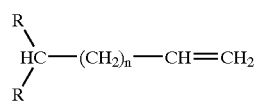

where each R is an alkyl group, and n is an integer which can be zero.
3) Linear internal olefins are compounds of the formulas

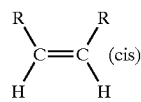 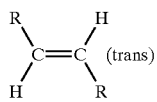

where each R is an alkyl group.

4) Tri-substituted olefins are compounds of the formula

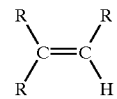

where each R is an alkyl group. It will be noted that tri-substituted olefins do have an internal double bond and thus are a special type of internal olefins.

The α-olefin mixtures used in the practice of this invention will typically contain (a) at least one $C_{10-20}$ vinylidene olefin and (b) at least one $C_{10-20}$ linear 1-olefin or (c) at least one $C_{10-20}$ remotely-branched 1-olefin, or (d) a combination of at least (a), (b), and (c), and optionally (e) at least one $C_{10-20}$ internal olefin or (f) at least one saturated hydrocarbon, or (g) both of (e) and (f). Preferably, the olefins present in the initial mixture have in the range of about 12 to about 16 carbon atoms permolecule. A particularly preferred starting mixture of olefins is one in which the olefins are substantially entirely $C_{14}$ olefins. The saturated hydrocarbon if present can be present as an impurity or it can be present as an inert diluent or solvent. Usually the use of a separate solvent is unnecessary unless the α-olefin mixture to be used contains undissolved solid components.

The conditions used in carrying out the selective isomerization pursuant to this invention can be varied within reasonable limits. Typically the amount of anhydrous hydrogen bromide used will be in the range of about 0.05 mole to about 1.5 moles per mole of olefins present in the initial olefin mixture being used in the process. Desirably, this amount is in the range of about 0.05 mole to about 0.4 mole of hydrogen bromide or in the range of about 0.1 to about 0.4 mole of hydrogen bromide per mole of olefins present in the olefin mixture. Preferred proportions are in the range of about 0.05 mole to about 0.3 mole of hydrogen bromide per mole of olefins present in the initial olefin mixture.

Typically the isomerization is performed with the isomerization mixture or reactor contents at a temperature in the range of about −20° C. to about 100° C., and preferably at a temperature in the range of about 10° C. to about 50° C. A particularly preferred embodiment involves performing the isomerization with the isomerization mixture or reactor contents at a temperature in the range of about 20° C. to about 30° C.

The time period during which the isomerization is carried out is typically less than about 100 minutes and preferably is less than about 20 minutes. It is particularly preferred to carry out the isomerization in a period of up to 5 minutes, e.g., during a period in the range of about 1 to about 5 minutes.

In carrying out the isomerization, it is preferred to feed the olefins and the anhydrous HBr in the absence of molecular oxygen (air, etc.), and free radical initiator into a plug flow reactor. As is well known, reactors of this type are designed to enable all of the reaction components to flow as a stream through the reactor ideally at the same or essentially the same velocity with minimal back-mixing. For further details concerning plug flow reactors, one may refer for example to Octave Levenspiel, *Chemical Reaction Engineering*, 2nd Edition, John Wiley & Sons, Pub., Copyright 1972, pages 97 and 107–115.

If it is desired to remove the HBr from the product of the olefin isomerization, this can be done very efficiently simply by passing the reaction product into and through a water scrubber to dissolve the HBr from the product mixture. If desired, the purified isomerized olefins can then be dried before being stored or put to use. If on the other hand the product from the isomerization is to be used in the manufacture of amines by an improved process of this invention, removal of the HBr is unnecessary as the next step in the process is hydrobromination. Thus the HBr used in the isomerization can be left in the product mixture so as to form part of the HBr used in the hydrobromination. To this extent such HBr would serve a dual role in the process.

The practice and advantages of this invention are illustrated by the following Examples which are not intended to limit the scope of this invention to the particular conditions described therein.

EXAMPLES 1–5

A series of experiments were carried out using a commercially produced mixture of $C_{14}$ α-olefins containing approximately 75–80 wt % of linear 1-olefin and about 17 wt % of vinylidene olefin (BP-Amoco). All experiments were carried out in a plug flow reactor under anhydrous conditions and in the absence of any form of molecular oxygen (whether air or otherwise) and free radical initiator. In runs carried out pursuant to this invention (Examples 1–5), known quantities of anhydrous hydrogen bromide and known quantities of the olefin mixture were fed into the reactor using a predetermined residence time. Each reaction was performed by feeding the components into the reactor while the components were at room temperature. The products were washed in a water scrubber to remove the HBr. A control run was carried out in the same manner except that no HBr was used. In all cases, the effluents from the reactor were collected and subjected to GC analysis and in some cases to NMR analysis. Conditions and results of these experiments are summarized in the following Table in which the following abbreviations are used for the components identified in the analyses:

2-hexyl is 2-hexyl-1-octene, a vinylidene olefin;

2-butyl is 2-butyl-1-decene, a vinylidene olefin, 2-ethyl is 2-ethyl-1-dodecene, a vinylidene olefin;

1-tetra is 1-tetradecene, a linear 1-olefin, 2-trans is trans-2-tetradecene, an internal linear olefin; and 2-cis is cis-2-tetradecene, an internal linear olefin.

"exclusion" should not be taken as an absolute. If some small amount of oxygen molecules is present in the reactor the question is: Will their presence do any significant harm to the overall operation? If an amount of molecular oxygen is present that does not affect either the process or the results obtained from the process in any materially significant adverse way, such amount is permissible and within the scope of this invention.

These same considerations apply to the specified absence in the reaction of free radical initiator. These materials of course are such things as ozone, ozonides, peroxides, hydroperoxides, persulfates, azo compounds, etc., that are known to initiate the generation of free radicals in a chemical system. One should not add, or permit the presence of, a free radical initiator to the mixture in an amount that will result in hydrobromination occurring in amounts that form greater than about 1 wt % of hydrobrominated compounds based on the total weight of the product recovered from the isomerization reactor. Therefore, if traces of free radical initiators find their way into the isomerization reactor in amounts that result in no more than about 1 wt % of hydrobrominated compounds being formed in the product, such amount can be tolerated pursuant to this invention.

The term "anhydrous" is applied herein to the hydrogen bromide and conditions used in conducting the isomerization process. Trace amounts of water that do not adversely affect the conduct of the process or the results of the process can be tolerated pursuant to this invention. Again we are not dealing with absolutes. All that is required is that water is not allowed or caused to enter the system in an amount that would interfere with the isomerization reaction or adversely affect the results obtained from the isomerization process. Normal precautions along these lines will usually suffice. Moreover if need be, one can easily determine by test, whether the materials and conditions used are anhydrous enough to perform the present isomerization process without the occurrence of material adverse consequences. If need be, suitable known methods of dehydrating the materials to be fed to the reactor can be used.

Similarly, reference herein to "little if any hydrobromination occurs" or terms of similar import simply mean that the complete absence of hydrobromination during the isomerization reaction, while desirable, is not a requirement. Experiments to date have indicated that as long as the

TABLE

| | | | GC Area % | | | | |
|---|---|---|---|---|---|---|---|
| GC Retention time, minutes | Compound | Control, $C_{14}$ Olefin | Ex. 1 | Ex. 2 | Ex. 3 | Ex. 4 | Ex. 5 |
| 15.29 | 2-hexyl | 3.0 | 2.6 | 2.3 | 1.7 | 1.9 | 2.4 |
| 15.50 | 2-butyl | 4.9 | 4.3 | 3.9 | 1.5 | 3.2 | 4.0 |
| 16.41 | 2-ethyl | 9.2 | 7.4 | <1.2* | <1.6* | <3.1* | 6.2 |
| 16.70 | 1-tetra | 74.8 | 75.5 | 80.1 | 78.7 | 76.9 | 75.4 |
| 17.08 | 2-trans | 3.1 | 3.3 | 3.7 | 3.5 | 3.5 | 3.4 |
| 17.20 | Unknown | 0.02 | 0.8 | 1.7 | 2.3 | 2.3 | 1.4 |
| 17.50 | 2-cis | 1.7 | 1.8 | 2.0 | 1.9 | 1.9 | 1.9 |
| Wt % HBr in olefin | | | 2 | 4 | 8 | 4 | 2 |
| Residence time, minutes | | | 0.7 | 0.5 | 0.2 | 1.0 | 1.6 |
| Vinylidene by NMR, % | | 16.0 | 11.6 | 6.75 | | | 9.2 |

*It appears that some interferences occurred in this GC analysis, probably from trisubstituted olefins formed by the isomerization, which limited the accuracy of this analysis. Similar problems may be occurring on the 2-hexyl and 2-butyl analyses. NMR is deemed the more accurate analysis.

A few additional comments are deemed appropriate. Reference is made in this document to conducting the isomerization in the absence of, or by excluding, molecular oxygen, whether in the form of air or otherwise. Such "absence" or process is carried out properly in accordance with this disclosure, it is extremely unlikely that more than about 1 wt % of the product from the isomerization reactor will be hydrobrominated to 1-bromoalkanes. Such an amount of hydrobrominated product is desirably small and will not adversely affect the process from either a technical or economic standpoint. Thus such an amount of hydrobromination is acceptable pursuant to this invention. Preferably, the amount of hydrobrominated compounds, if any, in the product from the isomerization is 0.5 wt % or less.

It has also been stated herein that the linear 1-olefins and the remotely branched 1-olefins are substantially unaffected in the isomerization process. Likewise it has been stated in connection with the improvement in producing amines, in selectively dehydrobrominating the bromoalkanes the 1-bromoalkanes are substantially unaffected. The use of the term "substantially" takes cognizance of the fact that in chemical reactions unexplainable small variations in results can take place from run to run or from time to time. Thus it cannot be correctly stated herein that absolutely none of the linear 1-olefins and the remotely branched 1-olefins or that absolutely none of the 1-bromoalkanes will be affected. In fact, amounts of isomerized bromoalkanes of up to about 3 wt % may be formed, and such small amounts are entirely acceptable. The actual amount of such isomerized bromoalkanes can easily be determined by chemical and/or instrumental analysis of the product. If the amount that is affected has no material effect upon the economic viability of the process in which it is conducted, it is acceptable and is within the scope of this invention.

As one can readily appreciate, there are a vast number of embodiments of this invention. A case in point relates to the improved process for producing amine from a mixture of α-olefins that comprise vinylidene olefins and 1-olefins. It will be recalled that this process is as follows:

A) In a process for producing amine from a mixture of α-olefins comprising vinylidene olefins and 1-olefins, which process comprises:
   a) subjecting the mixture of olefins to selective isomerization to convert vinylidene olefins to tri-substituted olefins;
   b) hydrobrominating olefin mixture resulting from the isomerization to form bromoalkanes comprising 1-bromoalkanes and secondary bromoalkanes;
   c) selectively dehydrobrominating the bromoalkanes whereby 1-bromoalkanes are substantially unaffected and secondary bromoalkanes are converted to olefins;
   d) aminating the bromoalkanes with an amine having at least one replaceable hydrogen atom whereby 1-bromoalkanes are converted to one or more amine hydrobromides; and
   e) converting the amine hydrobromides into one or more amines;
   the improvement which comprises effecting said selective isomerization by contacting said mixture of α-olefins with anhydrous hydrogen bromide in a reaction zone under anhydrous conditions and in the absence of molecular oxygen and free radical initiator for a period of time sufficient to selectively isomerize vinylidene olefin to tri-substituted olefin.

Among the embodiments pertaining to this process are the following:

B) A process as in A) wherein the mixture of α-olefins comprises (i) at least one $C_{10-20}$ vinylidene olefin, (ii) at least one $C_{10-20}$ linear 1-olefin or (iii) at least one $C_{10-20}$ remotely-branched 1-olefin, or (iv) a combination of (i), (ii) and (iii), and optionally (v) at least one $C_{10-20}$ internal olefin or (vi) at least one saturated hydrocarbon, or (vii) both of (v) and (vi).

C) A process as in A) or B) wherein said period of time is less than about 100 minutes.

D) A process as in A) or B) wherein the hydrogen bromide and the mixture of α-olefins are fed into and contact each other in said reaction zone, and wherein the proportions of the feeds are in the range of about 0.05 mole to about 1.5 moles of hydrogen bromide fed per mole of olefins fed.

E) A process as in A) or B) wherein the hydrogen bromide and the mixture of α-olefins are fed into and contact each other in said reaction zone; wherein the isomerization is performed with the temperature in said reaction zone being in the range of about −20° C. to about 100° C.

F) A process as in A) or B) wherein the hydrogen bromide and the mixture of α-olefins are fed into and contact each other in said reaction zone; wherein the proportions of the feeds are in the range of about 0.05 mole to about 1.5 moles of hydrogen bromide fed per mole of olefins fed; wherein the isomerization is performed with the temperature in said reaction zone being in the range of about −20° C. to about 100° C.; and wherein said period of time is less than about 100 minutes.

G) A process as in A) or B) wherein the hydrogen bromide and the mixture of α-olefins are fed into and contact each other in said reaction zone; wherein the proportions of the feeds are in the range of about 0.1 mole to about 0.4 mole of hydrogen bromide fed per mole of olefins fed; wherein the isomerization is performed with the temperature in said reaction zone being in the range of about 10° C. to about 50° C.; and wherein said period of time is less than about 20 minutes.

H) A process as in A) or B) wherein the olefins present in the mixture of α-olefins have in the range of about 12 to about 16 carbon atoms per molecule.

I) A process as in H) wherein the hydrogen bromide and the olefins are fed into and contact each other in said reaction zone; wherein the proportions of the feeds are in the range of about 0.05 mole to about 1.5 moles of hydrogen bromide fed per mole of olefins fed; wherein the isomerization is performed with the temperature in said reaction zone being in the range of about −20° C. to about 100° C.; and wherein said period of time is less than about 100 minutes.

J) A process as in H) wherein the hydrogen bromide and the olefins are fed into and contact each other in said reaction zone; wherein the proportions of the feeds are in the range of about 0.1 mole to about 0.4 mole of hydrogen bromide fed per mole of olefins fed; wherein the isomerization is performed with the temperature in said reaction zone being in the range of about 10° C. to about 50° C.; and wherein said period of time is less than about 20 minutes.

K) A process as in J) wherein said temperature is in the range of about 20° C. to about 30° C., and wherein said period of time is in the range of about 1 to about 5 minutes.

L) A process as in A) or B) wherein the olefins present in said mixture consist essentially of olefins having 14 carbon atoms per molecule.

M) A process as in L) wherein the hydrogen bromide and the mixture of α-olefins are fed into and contact each other in said reaction zone, wherein the proportions of the feeds are in the range of about 0.05 mole to about 1.5 moles of hydrogen bromide fed per mole of olefins fed, wherein the isomerization is performed with the temperature in said reaction zone being in the range of about −20° C. to about 100° C.; and wherein said period of time is less than about 100 minutes.

N) A process as in L) wherein the hydrogen bromide and the mixture of α-olefins are fed into and contact each other in said reaction zone, wherein the proportions of the feeds are in the range of about 0.1 mole to about 0.4 mole of hydrogen bromide per mole of olefins fed; wherein the isomerization is performed with the temperature in said reaction zone being in the range of about 10° C. to about 50° C.; and wherein said period of time is less than about 20 minutes.

O) A process as in N) wherein said temperature is in the range of about 20° C. to about 30° C., and wherein said period of time is in the range of about 1 to about 5 minutes.

P) A process as in any of A), B), H), or L) wherein the hydrogen bromide and the mixture of α-olefins are fed into and contact each other in said reaction zone; wherein the proportions of the feeds are in the range of about 0.05 mole to about 0.3 mole of hydrogen bromide per mole of olefins present in the mixture of α-olefins; wherein the isomerization is performed with the temperature in said reaction zone being in the range of about 20° C. to about 50° C.; and wherein said period of time is up to about 5 minutes.

Q) A process as in any of A) through P) wherein the isomerization is performed in a plug-flow reactor.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Thus, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that the substance, component or ingredient may have lost its original identity through a chemical reaction or transformation during the course of such contacting, blending or mixing operations is thus wholly immaterial for an accurate understanding and appreciation of this disclosure and the claims thereof Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of isomerizing at least one vinylidene olefin to at least one tri-substituted olefin, which process comprises contacting the vinylidene olefin with anhydrous hydrogen bromide under anhydrous conditions and in the absence of molecular oxygen and free radical initiator, said contacting being for a period of time sufficient to isomerize vinylidene olefin to tri-substituted olefin.

2. A process as in claim 1 wherein said vinylidene olefin is isomerized to tri-substituted olefin while in the presence of at least one olefin other than vinylidene olefin.

3. A process as in claim 1 or 2 wherein said contacting takes place in a plug flow reactor.

4. A process for selective isomerization of at least one $C_{10\text{-}20}$ vinylidene olefin to tri-substituted olefin in an anhydrous hydrocarbon mixture comprised of (i) at least one $C_{10\text{-}20}$ vinylidene olefin, (ii) at least one $C_{10\text{-}20}$ linear 1-olefin or (iii) at least one $C_{10\text{-}20}$ remotely-branched 1-olefin, or (iv) a combination of (i), (ii) and (iii), and optionally (v) at least one $C_{10\text{-}20}$ internal olefin or (vi) at least one saturated hydrocarbon, or (vii) both of (v) and (vi), while leaving the 1-olefins substantially unaffected during the isomerion, which process comprises contacting the mixture with anhydrous hydrogen bromide under anhydrous conditions and in the absence of molecular oxygen and free radical initiator for a period of time sufficient to selectively isomerize vinylidene olefin to tri-substituted olefin.

5. A process as in claim 4 wherein said period of time is less than about 100 minutes.

6. A process as in claim 4 wherein the isomerization is performed at one or more temperatures in the range of about −20° C. to about 100° C.

7. A process as in any of claims 4–6 wherein the isomerization is performed in a plug flow reactor.

8. A process as in claim 4 wherein the hydrogen bromide and the hydrocarbon mixture are fed into and contact each other in a reaction zone, and wherein the proportions of the feeds are in the range of about 0.05 mole to about 1.5 moles of hydrogen bromide per mole of olefins.

9. A process as in claim 4 wherein the hydrogen bromide and the hydrocarbon mixture are fed into and contact each other in a reaction zone; wherein the proportions of the feeds are in the range of about 0.05 mole to about 1.5 moles of hydrogen bromide per mole of olefins; wherein the isomerization is performed with the temperature in said reaction zone being in the range of about −20° C. to about 100° C.; and wherein said period of time is less than about 100 minutes.

10. A process as in claim 4 wherein the hydrogen bromide and the hydrocarbon mixture are fed into and contact each other in a reaction zone; wherein the proportions of the feeds are in the range of about 0.1 mole to about 0.4 mole of hydrogen bromide per mole of olefins; wherein the isomerization is performed with the temperature in said reaction zone being in the range of about 10° C. to about 50° C.; and wherein said period of time is less than about 20 minutes.

11. A process as in any of claims 8–10 wherein the reaction zone is in a plug-flow reactor.

12. A process as in claim 4 wherein the olefins present in said mixture have in the range of about 12 to about 16 carbon atoms per molecule.

13. A process as in claim 12 wherein the isomerization is performed in a plug flow reactor.

14. A process as in claim 12 wherein the hydrogen bromide and the olefins are fed into and contact each other in a reaction zone; wherein the proportions of the feeds are in the range of about 0.05 mole to about 1.5 moles of hydrogen bromide per mole of olefins; wherein the isomerization is performed with the temperature in said reaction zone being in the range of about −20° C. to about 100° C.; and wherein said period of time is less than about 100 minutes.

15. A process as in claim 12 wherein the hydrogen bromide and the olefins are fed into and contact each other in a reaction zone; wherein the proportions of the feeds are in the range of about 0.1 mole to about 0.4 mole of hydrogen bromide per mole of olefins; wherein the isomerization is performed with the temperature in said reaction zone being in the range of about 10° C. to about 50° C.; and wherein said period of time is less than about 20 minutes.

16. A process as in claim 15 wherein said temperature is in the range of about 20° C. to about 30° C., and wherein said period of time is in the range of about 1 to about 5 minutes.

17. A process as in any of claims 14–16 wherein the reaction zone is in a plug-flow reactor.

18. A process as in claim 4 wherein the olefins present in said hydrocarbon mixture consist essentially of olefins having 14 carbon atoms per molecule.

19. A process as in claim 18 wherein the isomerization is performed in a plug flow reactor.

20. A process as in claim 18 wherein the hydrogen bromide and the hydrocarbon mixture are fed into and contact each other in a reaction zone; wherein the proportions of the feeds are in the range of about 0.05 mole to about 1.5 moles of hydrogen bromide per mole of olefins; wherein the isomerization is performed with the temperature in said reaction zone being in the range of about −20° C. to about 100° C.; and wherein said period of time is less than about 100 minutes.

21. A process as in claim 18 wherein the hydrogen bromide and the hydrocarbon mixture are fed into and contact each other in a reaction zone; wherein the proportions of the feeds are in the range of about 0.1 mole to about 0.4 mole of hydrogen bromide per mole of olefins; wherein the isomerization is performed with the temperature in said reaction zone being in the range of about 10° C. to about 50° C.; and wherein said period of time is less than about 20 minutes.

22. A process as in claim 21 wherein said temperature is in the range of about 20° C. to about 30° C., and wherein said period of time is in the range of about 1 to about 5 minutes.

23. A process as in any of claims 20–22 wherein the reaction zone is in a plug-flow reactor.

24. A process as in any of claims 4, 12, or 18 wherein the hydrogen bromide and the hydrocarbon mixture are fed into and contact each other in a reaction zone; wherein the proportions of the feeds are in the range of about 0.05 mole to about 0.3 mole of hydrogen bromide per mole of olefins; wherein the isomerization is performed with the temperature in said reaction zone being in the range of about 20° C. to about 50° C., and wherein said period of time is up to about 5 minutes.

25. A process as in claim 24 wherein the reaction zone is in a plug-flow reactor.

26. In a process for producing amine from a mixture of α-olefins comprising vinylidene olefins and 1-olefins, which process comprises:

a) subjecting the mixture of olefins to selective isomerization to convert vinylidene olefins to tri-substituted olefins, b) hydrobrominating olefin mixture resulting from the isomerization to form bromoalkanes comprising 1-bromoalkanes and secondary bromoalkanes and/or tertiary bromoalkanes;

c) selectively dehydrobrominating bromoalkanes resulting from b) whereby 1-bromoalkanes are substantially unaffected and secondary and/or tertiary bromoalkanes present are converted to olefins;

d) aminating bromoalkanes from c) with an amine having at least one replaceable hydrogen atom whereby 1-bromoalkanes are converted to one or more amine hydrobromides; and e) converting amine hydrobromides from d) into one or more amines;

the improvement which comprises effecting said selective isomerization by contacting said mixture of α-olefins with anhydrous hydrogen bromide under anhydrous conditions and in the absence of molecular oxygen and free radical initiator for a period of time sufficient to selectively isomerize vinylidene olefin to tri-substituted olefin.

27. The improvement as in claim 26 wherein the selective isomerization is performed in a plug-flow reactor.

* * * * *